(12) United States Patent
Tseng et al.

(10) Patent No.: US 11,574,446 B2
(45) Date of Patent: Feb. 7, 2023

(54) DIGITAL IMAGE REALITY ALIGNING KIT AND METHOD APPLIED TO MIXED REALITY SYSTEM FOR SURGICAL NAVIGATION

(71) Applicant: National Central University, Taoyuan (TW)

(72) Inventors: Ching Shiow Tseng, Taoyuan (TW); Te-Hsuan Feng, Taoyuan (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 597 days.

(21) Appl. No.: 16/690,319

(22) Filed: Nov. 21, 2019

(65) Prior Publication Data
US 2021/0059760 A1 Mar. 4, 2021

(30) Foreign Application Priority Data

Aug. 30, 2019 (TW) ................................. 108131367
Aug. 30, 2019 (TW) ................................. 108131391

(51) Int. Cl.
*G06T 19/00* (2011.01)
*A61B 34/20* (2016.01)
*G06T 19/20* (2011.01)

(52) U.S. Cl.
CPC ............ *G06T 19/006* (2013.01); *A61B 34/20* (2016.02); *G06T 19/20* (2013.01); *A61B 2034/2055* (2016.02); *A61B 2034/2068* (2016.02)

(58) Field of Classification Search
None
See application file for complete search history.

(56) References Cited

U.S. PATENT DOCUMENTS

| 2018/0071032 A1* | 3/2018 | de Almeida Barreto .................... G06T 19/006 |
| 2019/0254754 A1* | 8/2019 | Johnson ................. A61B 34/30 |
| 2020/0218345 A1* | 7/2020 | Liu ......................... G06F 3/013 |

FOREIGN PATENT DOCUMENTS

JP H1139506 A * 2/1999

* cited by examiner

*Primary Examiner* — Jwalant Amin
(74) *Attorney, Agent, or Firm* — Demian K. Jackson; Jackson IPG PLLC

(57) ABSTRACT

The present invention relates to a digital image reality aligning kit, applied to a mixed reality system integrated with a surgical navigation system including: a plurality of moveable markers corresponded to a plurality of moveable marker coordinates respectively and a part of the plurality of moveable markers configured on a surgical instrument; a positioning marker corresponded to a positioning marker coordinate and configured in proximity to a surgical area corresponded to a surgical area coordinate, when the positioning marker is settled, the relative position thereof with respect to the other part of the plurality of moveable markers and the surgical area are determined accordingly, so as to transform the surgical area coordinate to the positioning marker coordinate; and a mixed reality device corresponded to a mixed reality device coordinate and detecting the positioning marker to transform the positioning marker coordinate to the mixed reality device coordinate accordingly, so as to project a surgical area digital image corresponded to a surgical area digital image coordinate onto the surgical area.

7 Claims, 13 Drawing Sheets

DIGITAL IMAGE REALITY ALIGNING KIT AND METHOD APPLIED TO MIXED REALITY SYSTEM FOR SURGICAL NAVIGATION

CROSS-REFERENCE TO RELATED APPLICATION

The present application claims the priority benefits of both Taiwan invention patent application serial No. 108131367, dated August 30, and Taiwan invention patent application serial No. 108131391, dated August 30, filed in Taiwan intellectual property office. All contents disclosed in the above two Taiwan invention patent applications are incorporated herein by reference.

FIELD

The present invention relates to an aligning kit and method for aligning a digital image to a corresponding realistic object, in particular to a digital image reality aligning kit and method applied to a mixed reality system for surgical navigation.

BACKGROUND

Nowadays, there are still many high-risk surgeries, such as but not limited to: a craniotomy, an arterial embolization surgery, a minimally invasive surgery, and a spinal surgery. All of these surgeries have the same problems, such as: difficulties to precisely position, high level of operation difficulty, high technicality required, and highly complexity. These problems are resulted from that a surgeon fails to actually see the surgical area during the operation visually, but just sees a minor portion of the surgical area or outer layer tissues thereof, directly resulting in very high risk for the surgery to operate.

In view of the abovementioned reasons, prior to the execution of these high-risk surgeries, typically the surgeons must utilize, such as: the X-ray imaging technique, the computed tomography (CT) technique, the computed tomography angiography (CTA) technique, the digital subtraction angiography (DSA) technique, the maximum intensity projection (MIP) technique, or the magnetic resonance imaging (MRI) technique to film a series of 2D slice images for a surgical area in advance. Then surgeons view and refer to these images at times before and during the operation, and speculate and imagine the actual state and condition of the surgical area according to their own expertise and experience to execute and complete the entire surgery. Thus it is conceivable the difficulty for these high-risk surgeries, and the mental stress the surgeons endure in executing and operating these high-risk surgeries.

Therefore, in order to enable surgeons to visually see the reality, and to manage the actual state and condition of surgical area easily and intuitively before and during the surgery, the same applicant of this case ever proposed a real-time and dynamic mixed realty system capable of integrating with a surgical navigation system, to project a digital model for the surgical area including the blood vessels, nerves, brain tissues, lesions and surgical instruments onto the surgical area directly by using a mixed reality (MR) technique, so that the surgeons can manage the actual state of surgical area and the surgical progress at any time in an intuitive way, before and during the surgery, so as to reduce the difficulty to operate the surgery and mitigate surgeon's stress.

However, in the abovementioned real-time and dynamic mixed realty system integrated with a surgical navigation system, in an open three-dimension space, how to align a virtual digital images of the surgical area to the surgical area accurately and dynamically in real time, and to correctly position the surgical area in the spatial space, is another critical technical issue required to overcome and deal with.

Hence, there is a need to solve the above deficiencies/issues.

SUMMARY

In view of the positioning and aligning issues existing in real-time and dynamic mixed realty system integrated with a surgical navigation system, the present invention provides two types of tracking markers with different functions for a mobile mixed reality wearable device and an immobile optical tracker respectively to position and track in real time, so as to determine the projection position of real-time dynamic 3D MR image, and to provide the real-time dynamic 3D MR images at different viewing angles.

Based on the aligning technique proposed by the present invention, the MR device can accurately project the 3D image containing the actual state of blood vessels, nerves and brain tissues in the patient's surgical area onto the surgical area by real-time 3D visualization, which is displayed by the MR device for the surgeon, no matter how the surgeon moves during the operation, the 3D image displayed by the MR device is always positioned in the surgical area accurately, and the 3D images of surgical area at different viewing angles are displayed instantly and dynamically as the surgeon's viewing angle changes, which can be seen by multiple surgeons in different positions at different viewing angles, so that multiple surgeons can take part in the complex surgery synchronously.

The aligning technique proposed by the present invention can be used as the core technology in the MR surgical navigation system, the images of surgical area, patient and surgical instrument are displayed instantly by the MR glasses, assisting the surgeon to plan a safe surgical approach more intuitively, 3D surgical navigation and reduce the risks of cerebral arterial injuries during of brain surgery.

The present invention provides a digital image reality aligning kit, applied to a mixed reality system integrated with a surgical navigation system, and including: a plurality of moveable markers corresponding to a plurality of moveable marker coordinates respectively and a part of the plurality of moveable markers configured on a surgical instrument; a positioning marker corresponded to a positioning marker coordinate and configured in proximity to a surgical area corresponded to a surgical area coordinate, when the positioning marker is settled, the relative position thereof with respect to the other part of the plurality of moveable markers and the surgical area are determined accordingly, so as to transform the surgical area coordinate to the positioning marker coordinate; and a mixed reality device corresponded to a mixed reality device coordinate and detecting the positioning marker to transform the positioning marker coordinate to the mixed reality device coordinate accordingly, so as to project a surgical area digital image corresponded to a surgical area digital image coordinate onto the surgical area Preferably, the digital image reality aligning kit further includes: a position tracker corresponded to a position tracker coordinate and sensing the plurality of moveable markers, so as to transform the plurality of moveable marker coordinates and the surgical area digital image coordinate to the surgical area coordinate in accordance with the position tracker coordinate Preferably, the digital image reality aligning kit further includes one of devices as follows: a first registered device configured in proximity to a surgical area and having a first surface and a second surface fixed with the first surface, wherein the first surface provides for the positioning marker to configure and the second surface provides for the other part of the plurality of moveable markers to configure, and when the first registered device is settled in proximity to the surgical area, the relative positions among the positioning marker, the other part of the plurality of moveable markers, and the surgical area are determined accordingly; and a second registered device configured in proximity to a surgical area and having a plurality of surfaces, wherein one of the plurality of surfaces provides for the positioning maker to configure and another one of the plurality of surfaces provides for the other part of the plurality of moveable markers to configure, and when the second registered device is settled in proximity to the surgical area, the relative positions among the positioning marker, the other part of the plurality of moveable markers, and the surgical area are determined accordingly.

Preferably, when the positioning marker, the other part of the plurality of moveable markers, and the surgical area are settled, the relative positions thereamong are determined accordingly, and thus the relationship of the coordinate transformation among the positioning marker coordinate, the plurality of moveable marker coordinates, and the surgical area coordinate are determined and acts as a system default.

Preferably, the surgical area digital image coordinate is transformed to the surgical area coordinate in accordance with the position tracker coordinate based on the plurality of moveable marker coordinates, to which the other part of the plurality of moveable markers correspond.

Preferably, the surgical area digital image coordinate is transformed to the position tracker coordinate by implementing an image registration algorithm, the positioning marker coordinate is transformed to the mixed reality device coordinate by implementing a pinhole perspective projection positioning algorithm.

Preferably, the surgical area digital image coordinate, the position tracker coordinate, the plurality of moveable marker coordinates, the positioning marker coordinate, the mixed reality device coordinate, and the surgical area coordinate are selected from one of a 2D Cartesian coordinate system, a 2D cylindrical coordinate system, a 2D spherical coordinate system, a 3D Cartesian coordinate system, a 3D cylindrical coordinate system, a 3D spherical coordinate system, and a combination thereof.

Preferably, the surgical area digital image is pre-constructed prior to an implementation of a surgery.

The present invention further provides a digital image reality aligning method, applied to a mixed reality system integrated with a surgical navigation system, and includes: providing a plurality of moveable markers corresponded to a plurality of moveable marker coordinates respectively, a positioning marker corresponded to a positioning marker coordinate, a mixed reality device corresponded to a mixed reality device coordinate, and a surgical area corresponded to a surgical area coordinate; configuring a part of the plurality of moveable markers onto a surgical instrument; configuring the positioning marker and the part of the plurality of moveable markers in proximity to the surgical area and determining the relative positions among the surgical area, the positioning marker, and the part of the plurality of moveable markers, so as to transform the surgical area coordinate to the positioning marker coordinate; and detecting the positioning marker through the mixed reality device, to transform the positioning marker coordinate to the mixed reality device coordinate accordingly, and to project a surgical area digital image onto the surgical area.

Preferably, the digital image reality aligning method further includes one of steps as follows: providing a position tracker corresponded to a position tracker coordinate and the surgical area digital image corresponded to a surgical area digital image coordinate; determining a position of the position tracker and detecting the plurality of moveable marker by the position tracker, so as to transform the plurality of moveable marker coordinates, to which the part of the plurality of moveable markers correspond, and the surgical area digital image coordinate to the surgical area coordinate in accordance with the position tracker coordinate; and determining the relationship of coordinate transformation among the positioning marker coordinate, the plurality of moveable marker coordinates, to which the part of the plurality of moveable markers correspond, and the surgical area coordinate, by determining the relative positions among the surgical area, the positioning marker, and the part of the plurality of moveable markers.

DESCRIPTION OF THE DRAWINGS

A more complete appreciation of the invention and many of the attendant advantages thereof are readily obtained as the same become better understood by reference to the following detailed description when considered in connection with the accompanying drawing, wherein.

DETAILED DESCRIPTION

Figure 1:
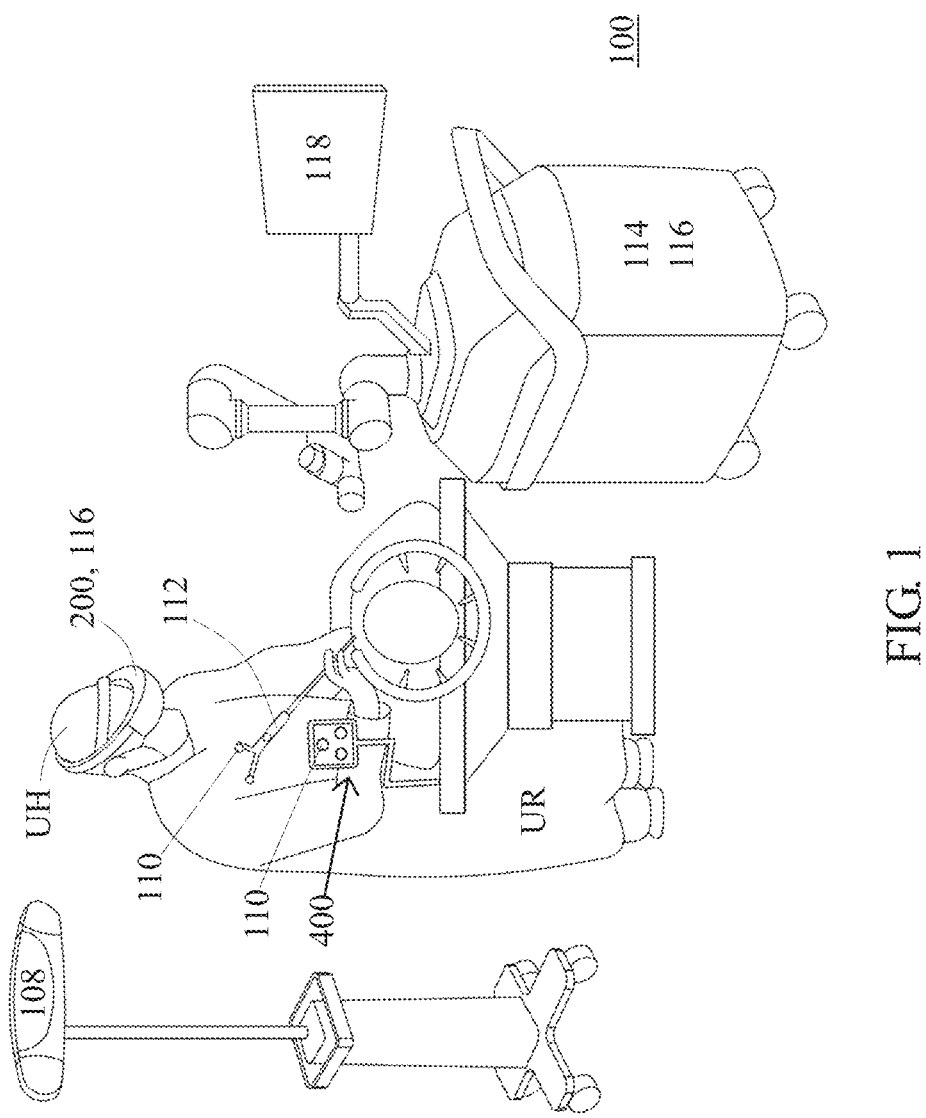
FIG. 1 is a diagram illustrating a fundamental architecture for the mixed reality system for surgical navigation, to which the digital image reality aligning kit and method in accordance with the present invention applies.

The present disclosure will be described with respect to particular embodiments and with reference to certain drawings, but the disclosure is not limited thereto but is only limited by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice.

It is to be noticed that the term "including", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device including means A and B" should not be limited to devices consisting only of components A and B.

The disclosure will now be described by a detailed description of several embodiments. It is clear that other embodiments can be configured according to the knowledge of persons skilled in the art without departing from the true technical teaching of the present disclosure, the claimed disclosure being limited only by the terms of the appended claims.

The mixed reality (MR) described in the present invention refers to the technology which uses precise calculation of location and angle of camera image, as well as image analysis technique, in combination and interaction with the virtual digital content on the screen and the real scenes. Virtual digital objects viewed by a user and displayed on the screen of the MR device, are correspondingly and accurately superposed and projected to actual articles, instruments, devices, or a surgical area in reality world where the user stays in, dynamically and interactively in real time. Preferably, the environmental parameters and information can be sensed by different sensors, and the real-time location and direction of virtual image corresponded to the real space are calculated accordingly; the display projects or superposes the virtual image onto the actual object in the reality. In addition, when the real environment and virtual environment are two ends of continuous system respectively, the display close to the real environment is also known as Augmented Reality (AR), while the display close to the virtual environment is also known as Virtual Reality (VR); the MR can be regarded as the synthetics of AR and VR.

Figure 2:
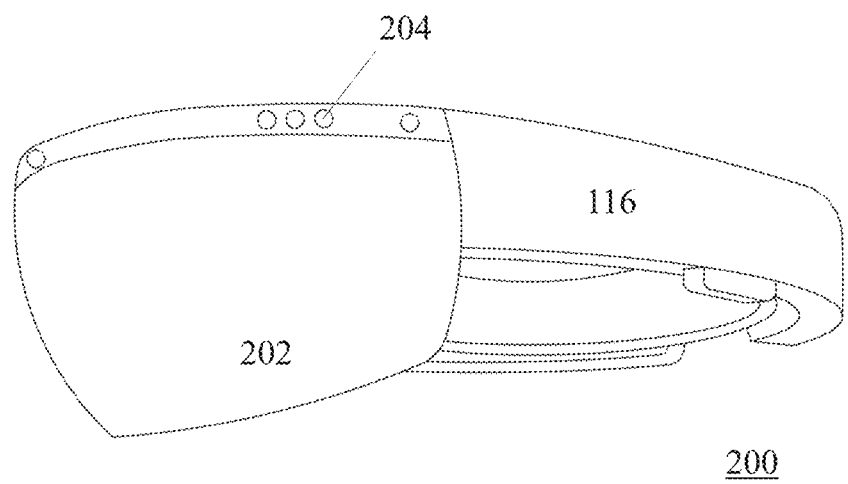
FIG. 2 is a diagram illustrating the MR device used in the system in accordance with the present invention.
Figure 3:
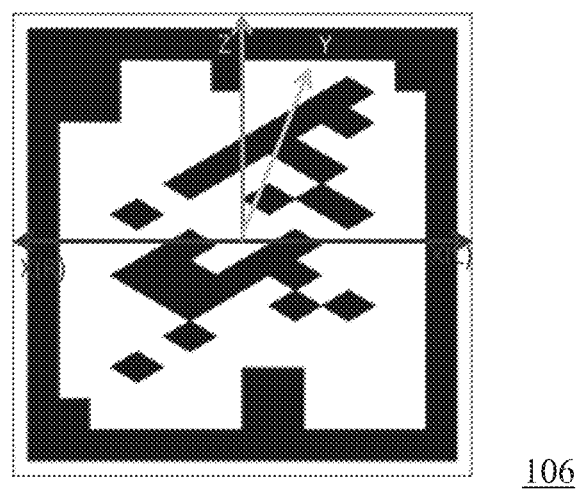
FIG. 3 is a diagram illustrating the positioning marker used in the system in accordance with the present invention.

FIG. 1 is a diagram illustrating a fundamental architecture for the mixed reality system for surgical navigation, to which the digital image reality aligning kit and method in accordance with the present invention applies. FIG. 2 is a diagram illustrating the MR device used in the system in accordance with the present invention. FIG. 3 is a diagram illustrating the positioning marker used in the system in accordance with the present invention. As shown in FIG. 1, the MR surgical navigation system 100 includes a MR device 200, a MR display 202, multiple MR sensors 204, a positioning marker 106, a position tracker 108, a moveable marker (position marker) 110, a surgical instrument 112, a computer 114, a computing unit module 116 and a panel display 118. In this embodiment, the MR device 200 is but not limited to Microsoft HoloLens device, worn on the head UH of a user UR. In this embodiment, the MR display 202 and MR sensor 204 are preferably configured on the same device, i.e. MR device 200, as shown in FIG. 2. The positioning marker 106 is a marker, for example, with a characteristic pattern, for the MR sensor 204 to read and identify, as shown in FIG. 3.

Figure 4:
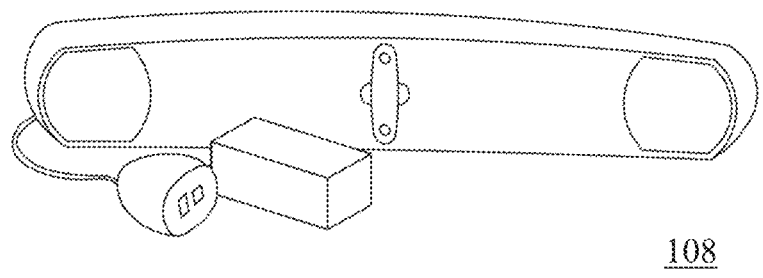
FIG. 4 is a diagram illustrating the position tracker used in the present invention.
Figure 5:
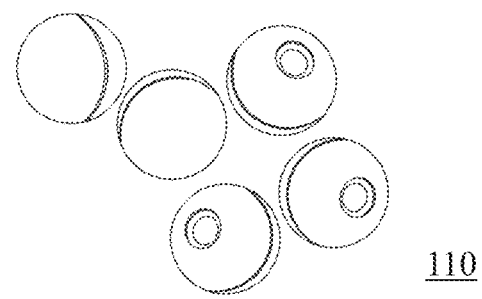
FIG. 5 is a diagram illustrating the moveable markers used in the present invention.
Figure 6:
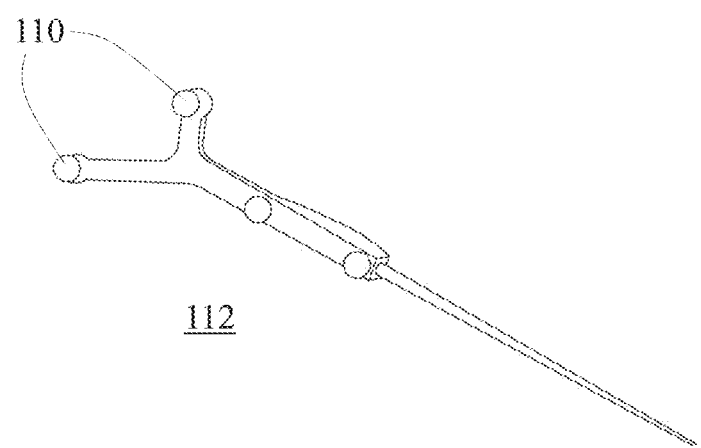
FIG. 6 is a diagram illustrating the surgical instrument equipped with location marker used in the present invention.

FIG. 4 is a diagram illustrating the position tracker used in the present invention. FIG. 5 is a diagram illustrating the moveable marker used in the present invention. FIG. 6 is a diagram illustrating the surgical instrument equipped with location marker used in the present invention. The position tracker 108 and moveable marker 110 coordinate with each other to track current position of different surgical instruments 112 instantly. In this embodiment, the position tracker 108 is preferably an infrared active optical tracker, as shown in FIG. 4, the moveable marker 110 is preferably a corresponding infrared passive reflective marker, designed and made into a sphere in diameter of about 1 cm, which can be embedded in the surgical instrument 112. As shown in FIG. 5 and FIG. 6, When the infrared scanning of position tracker 108 is actuated, the present space coordinate position of each moveable marker 110 can be tracked accurately in a pyramid-like 3D space and reported to the system continuously, so that the system can update the real-time spatial position of surgical instrument at any time.

Figure 7:
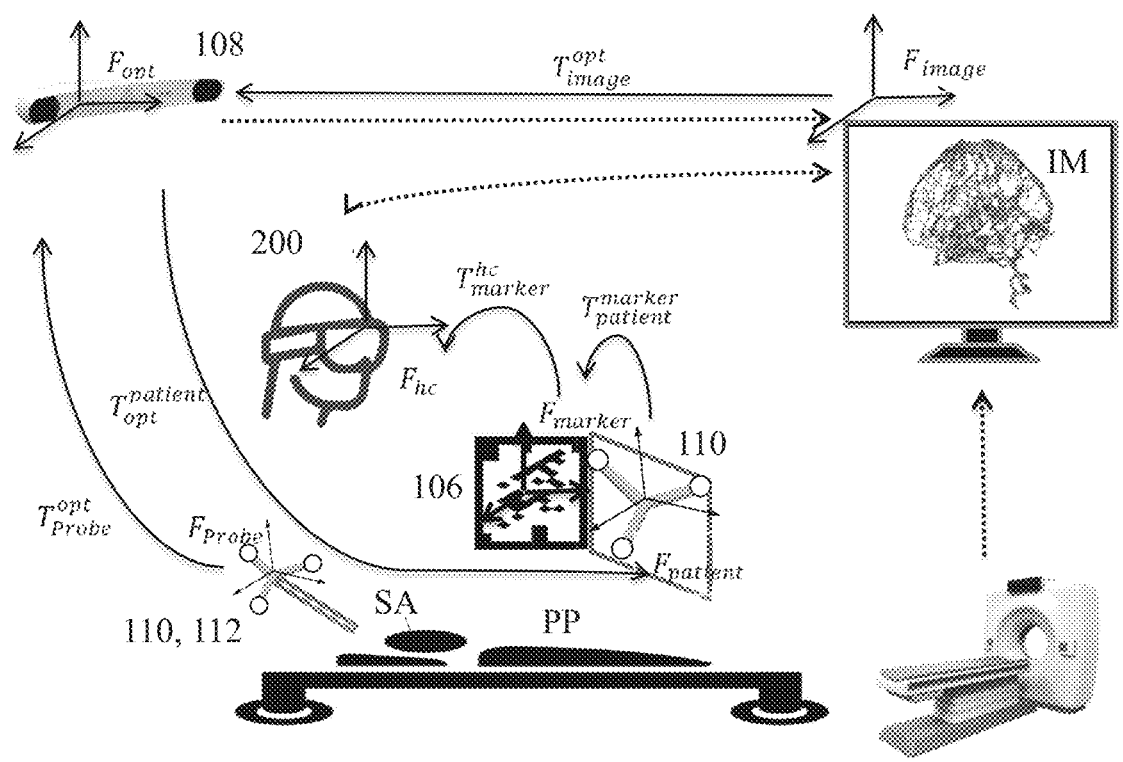
FIG. 7 is a diagram illustrating the multiple coordinates and the coordinate transformation thereof included in the mixed reality system for surgical navigation, to which the digital image reality aligning kit and method in accordance with the present invention applies.

FIG. 7 is a diagram illustrating the multiple coordinates and the coordinate transformation thereof included in the mixed reality system for surgical navigation, to which the digital image reality aligning kit and method in accordance with the present invention applies. FIG. 7 discloses the surgical area image model IM, surgical instrument 112, moveable marker 110, position tracker 108, surgical area SA, patient PP, positioning marker 106 and MR device 200. The surgical area image model IM is preferably to be made before surgery. It is a virtual 3D surgical area image composed of a series of preferably but not limited to CT slice images. The image content preferably contains the images of inner nerves, tissues, structures and organs of surgical area, regarded as the virtually augmented real surgical area.

Six coordinates independent of each other exist in the aforesaid MR surgical navigation system simultaneously, including surgical area image model coordinate frame $F_{image}$, moveable marker coordinate representing surgical instrument coordinate frame $F_{Probe}$, position tracker coordinate frame $F_{opt}$, surgical area coordinate frame $F_{patient}$, positioning marker coordinate frame $F_{marker}$ and MR device coordinate frame $F_{hc}$, listed in the following table.

| Symbol | Coordinate name |
|---|---|
| $F_{image}$ | Surgical area image model coordinate frame |
| $F_{Probe}$ | Surgical instrument coordinate frame (moveable marker coordinate frame) |
| $F_{opt}$ | Position tracker coordinate frame |
| $F_{patient}$ | Surgical area coordinate frame |
| $F_{marker}$ | Positioning marker coordinate frame |
| $F_{hc}$ | MR device coordinate frame |

In the aforesaid coordinates, the coordinate value of surgical area image model in the surgical area image model coordinate frame $F_{image}$ is given, when the position tracker, surgical area and positioning marker are located, the coordinate values of position tracker, surgical area and positioning marker in the position tracker coordinate frame $F_{opt}$, surgical area coordinate frame $F_{patient}$ and positioning marker coordinate frame $F_{marker}$ are determined respectively, becoming given values, and the coordinate transformation relationships among the surgical area image model coordinate frame $F_{image}$, position tracker coordinate frame $F_{opt}$ surgical area coordinate frame $F_{patient}$ and positioning marker coordinate frame $F_{marker}$ are determined accordingly. The coordinate values of the moveable marker installed on the surgical instrument and the MR device are variable, but the surgical area image model can be accurately aligned and projected onto the surgical area by using the position tracker positioning marker and positioning marker as anchored transformation point.

For the correspondence between surgical area image model and surgical area, the surgical area feature points can be correctly aligned to the corresponding points of image model by image and patient registration algorithm. e.g. Interactive Closest Point (ICP), the coordinate transformation relation of surgical area image model coordinate frame $F_{image}$ to position tracker coordinate frame $F_{opt}$ is obtained. As the transformation relation between the position tracker coordinate frame $F_{opt}$ and surgical area coordinate frame $F_{patient}$ is already known, the image model coordinate frame $F_{image}$, is transformed to surgical area coordinate frame $F_{patient}$ through position tracker coordinate frame $F_{opt}$, the basic correspondence between surgical area image model and surgical area position is completed.

For the correspondence between surgical instrument and surgical area, the coordinate value of surgical instrument in the position tracker coordinate frame $F_{opt}$ can be known by using the position tracker to track the moveable marker, meaning the surgical instrument coordinate frame $F_{Probe}$, is transformed to the position tracker coordinate frame $F_{opt}$. As the transformation relation between the position tracker coordinate frame $F_{opt}$ and the surgical area coordinate frame $F_{patient}$ is already known, the surgical instrument coordinate frame $F_{Probe}$ is transformed to the surgical area coordinate frame $F_{patient}$, the basic correspondence between surgical instrument and surgical area is completed.

For the coincidence relation between the MR device worn by the surgeon and the surgical area, the position tracker tracks the moveable marker of registered device, and the coordinate transformation relation between the moveable marker of registered device and the positioning marker is a preset design value, so that the surgical area coordinate frame $F_{patient}$ can be transformed by position tracker coordinate frame $F_{opt}$ to the positioning marker coordinate frame $F_{marker}$. The MR device preferably captures the positioning marker through the MR sensor, and then the real-time coordinate transformation relation between positioning marker coordinate frame $F_{marker}$ and MR device coordinate frame $F_{hc}$ can be calculated instantly by pinhole perspective projection localization algorithm, the surgical area image model can be accurately projected on the surgical area by the MR device.

The transformation of the above coordinate frames is described below

| Symbol | Coordinate transformation |
|---|---|
| $T_{image}^{opt}$ | Surgical area image model coordinate frame → position tracker coordinate frame (image and space transformation algorithm) |
| $T_{patient}^{marker}$ | Surgical area coordinate frame → positioning marker coordinate frame |
| $T_{marker}^{hc}$ | Positioning marker coordinate frame → MR device coordinate frame (pinhole perspective projection localization algorithm) |
| $T_{Probe}^{opt}$ | Surgical instrument coordinate frame → position tracker coordinate frame |
| $T_{opt}^{patient}$ | Position tracker coordinate frame → surgical area coordinate frame |

The key point of the aforesaid coordinate transformation is how to transform the coordinate frames of surgical instrument, surgical area and MR device, so as to accurately align the surgical area image model to the surgical area.

Figure 8:
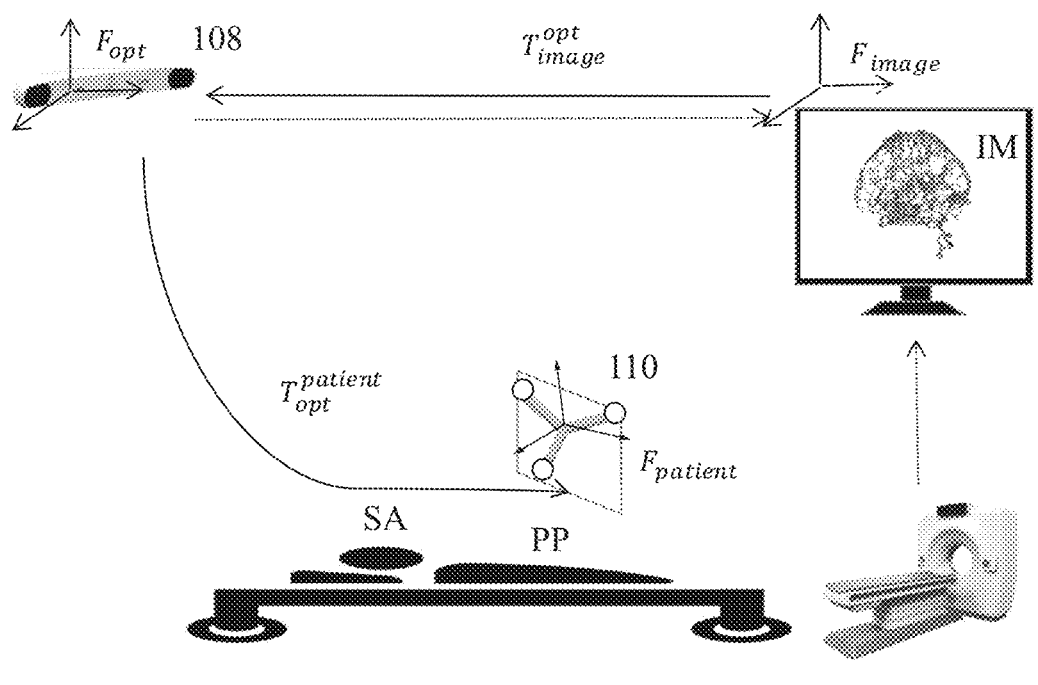
FIG. 8 is a diagram illustrating a relationship of coordinate transformation between the surgical area digital image model and the surgical area in accordance the present invention.
Figure 9:
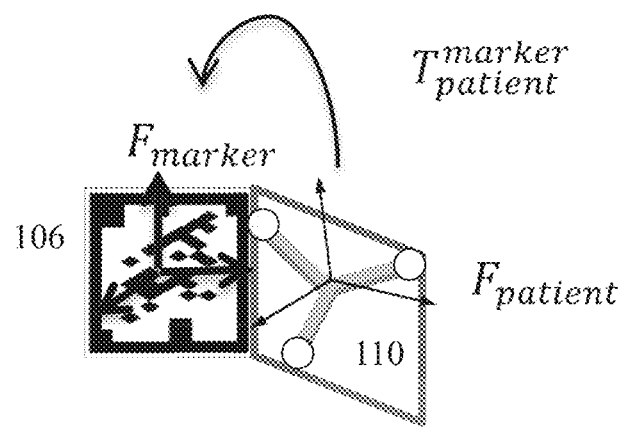
FIG. 9 is a diagram illustrating a relationship of coordinate transformation between the moveable markers on the registered device in proximity to the surgical area and the positioning marker in accordance with the present invention.
Figure 10:
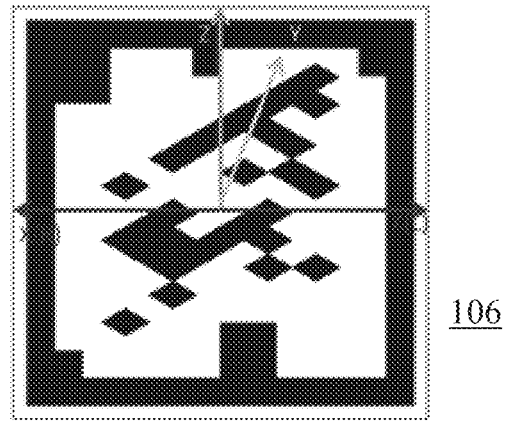
FIG. 10 is a diagram illustrating a definition of coordinate for the characteristic pattern contained in the positioning marker in accordance with the present invention.
Figure 11:
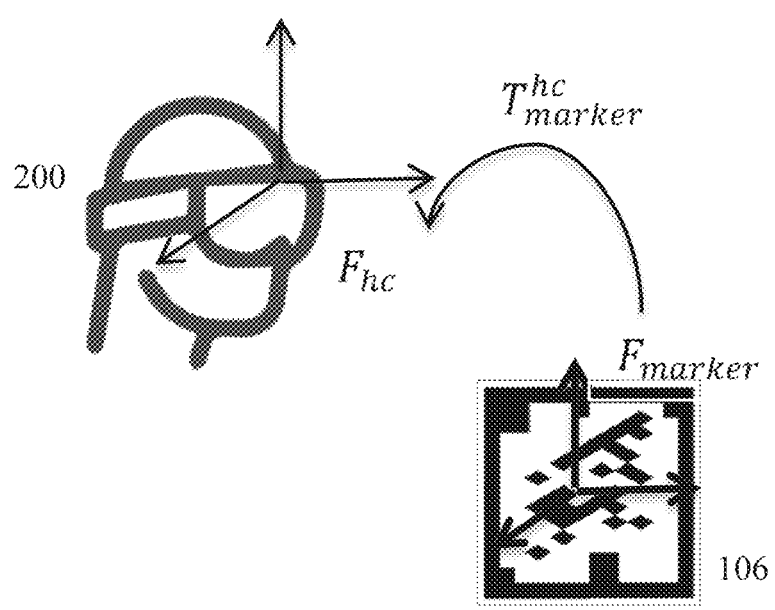
FIG. 11 is a diagram illustrating a relationship of coordinate transformation between the positioning marker and the mixed reality device in accordance with the present invention.
Figure 12:
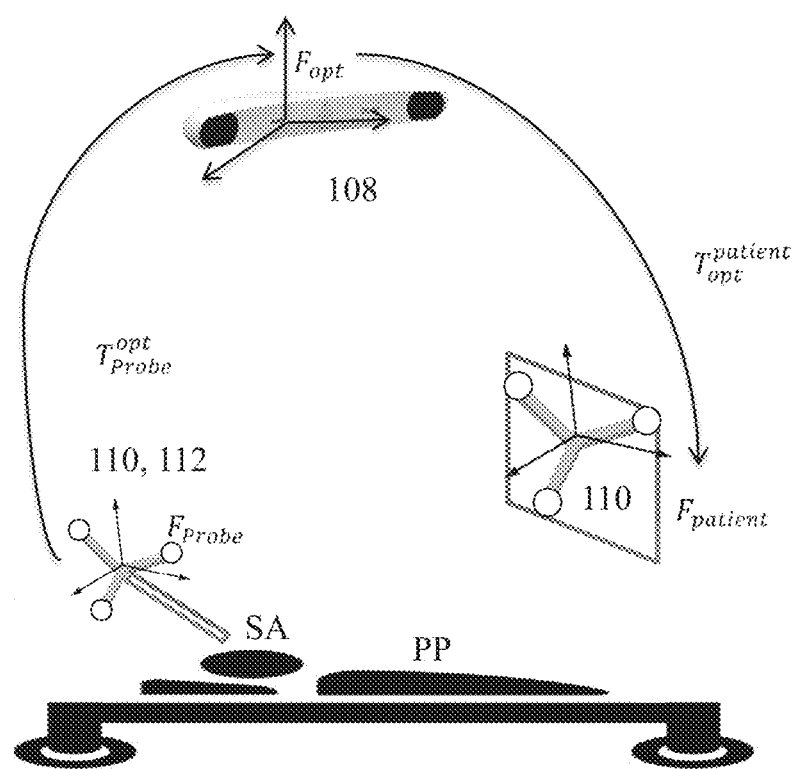
FIG. 12 is a diagram illustrating a relationship of coordinate transformation between the surgical instrument and the surgical area in accordance with the present invention.

FIG. 8 is a diagram illustrating a relationship of coordinate transformation between the surgical area image model and the surgical area in accordance the present invention. FIG. 9 is a diagram illustrating a relationship of coordinate transformation between the moveable makers on the registered device in proximity to the surgical area and the positioning marker in accordance with the present invention. FIG. 10 is a diagram illustrating a definition of coordinate for the characteristic pattern contained in the positioning marker in accordance with the present invention. FIG. 11 is a diagram illustrating a relationship of coordinate transformation between the positioning marker and the mixed reality device in accordance with the present invention. FIG. 12 is a diagram illustrating a relationship of coordinate transformation between the surgical instrument and the surgical area in accordance with the present invention.

The coordinate transformation relation between surgical area image model and surgical area (image and patient registration algorithm) is expressed as Eq. (1):

$$F_{image}^{patient} = T_{opt}^{patient} * T_{image}^{opt} * F_{image} \tag{1}$$

The coordinate transformation between surgical area image model and surgical area approximately includes five steps:

Step 1, as shown in FIG. 8, the main work before surgery is to capture the image of surgical area, e.g. CTA image, and then the 3D reconstruction of the image models using CTA image is performed according to a machine coordinate frame, so as to establish the patient's surgical area image model coordinate frame $F_{image}$.

Step 2, three image points on the patient's head image model are selected on $F_{image}$, the three corresponding points to the selected image points are selected on the patient's head by using the positioning instrument $F_{probe}$ with a moveable marker, the initial alignment of coordinate transformation is performed for the three image points and the three corresponding points, and then another N point coordinates are selected in the patient's head, the N point coordinates are transformed to the image coordinate frame $F_{image}$ by optimization method, e.g. ICP (Iterative Closest Point) algorithm, the average value of position errors to the corresponding image point coordinates is minimized, the optimum $T_{image}^{opt}$ is obtained, by the patient in known relative position (moveable marker) coordinate frame $F_{patient}$, $T_{opt}^{patient}$ is determined from $F_{opt}$, Eq. (2) is obtained.

Step 3, as shown in FIG. 9, the $T_{patient}^{marker}$ can be obtained from patient coordinate frame $F_{patient}$ and positioning marker coordinate frame $F_{marker}$ through the measurement of position tracker, Eq. (3) is obtained.

Step 4, as shown in FIG. 10, the coordinate is defined according to characteristic pattern.

Step 5, as shown in FIG. 11, the camera $F_{hc}$ uses monocular vision to locate $F_{marker}$ to obtain $T_{marker}^{hc}$, Eq. (4) is obtained by previous coordinate transformation, Eq. (5) is obtained at last.

$$T_{image}^{patient} = T_{opt}^{patient} * T_{image}^{opt} \qquad (2)$$

$$T_{image}^{marker} = T_{patient}^{marker} * T_{image}^{patient} \qquad (3)$$

$$T_{image}^{hc} = T_{marker}^{hc} * T_{image}^{marker} \qquad (4)$$

$$F_{hc} = T_{image}^{hc} * F_{image} \qquad (5)$$

The coordinate transformation between surgical instrument and surgical area approximately includes four steps:

Step 1: As shown in FIG. 12, the $T_{Probe}^{opt}$ is obtained from $F_{opt}$ according to the surgical instrument design value $F_{probe}$, and $T_{opt}^{patient}$ is obtained from $F_{opt}$ by patient coordinate frame $F_{patient}$, Eq. (6) is obtained by coordinate transformation.

Step 2: As shown in FIG. 9, $T_{marker}^{patient}$ can be obtained by patient coordinate frame $F_{patient}$ and positioning marker coordinate frame $F_{marker}$, and Eq. (7) can be obtained by instrument coordinate frame $F_{probe}$ and positioning marker coordinate $F_{marker}$.

Step 3: As shown in FIG. 10, the MR device $F_{hc}$ uses monocular vision to locate $F_{marker}$ to obtain $T_{marker}^{hc}$, Eq. (8) is derived from Eq. (7) and Eq. (9) is obtained at last.

$$T_{Probe}^{patient} = T_{opt}^{patient} * T_{Probe}^{opt} \qquad (6)$$

$$T_{Probe}^{marker} = T_{patient}^{marker} * T_{Probe}^{patient} \qquad (7)$$

$$T_{probe}^{hc} = T_{maker}^{hc} * T_{probe}^{marker} \qquad (8)$$

$$F_{hc} = T_{probe}^{hc} * F_{probe} \qquad (9)$$

Figure 13:
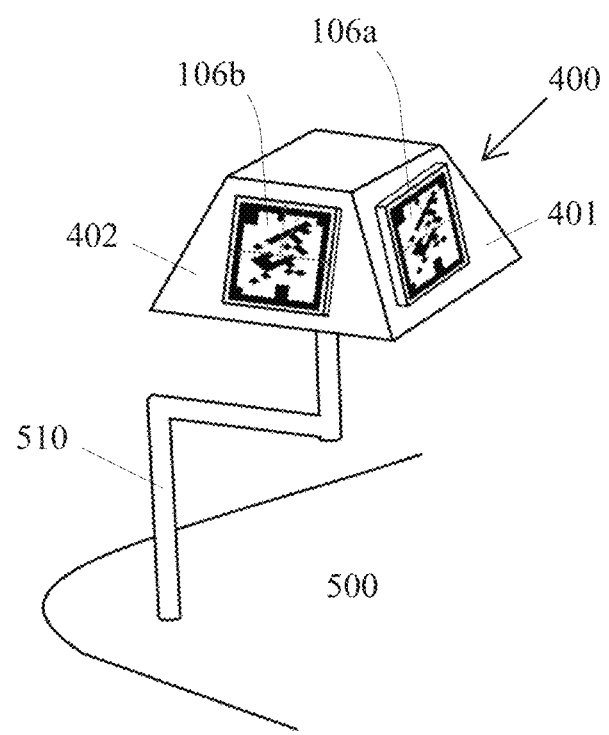
FIG. 13 is a perspective diagram viewed from a first angle of view illustrating a registered device with multiple surfaces used in the system in accordance with the present invention.
Figure 14:
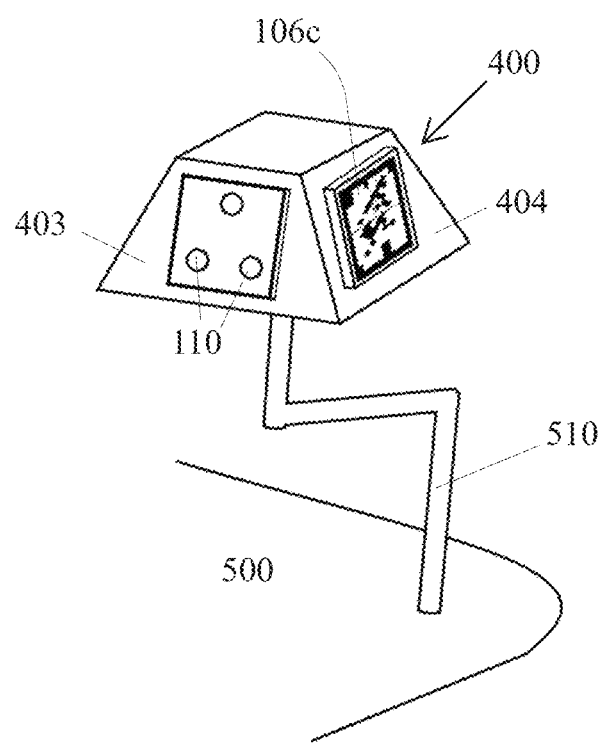
FIG. 14 is a perspective diagram viewed from a second angle of view illustrating a registered device with multiple surfaces used in the system in accordance with the present invention.

FIG. 13 is a perspective diagram viewed from a first angle of view illustrating a registered device with multiple surfaces used in the system in accordance with the present invention. FIG. 14 is a perspective diagram viewed from a second angle of view illustrating a registered device with multiple surfaces used in the system in accordance with the present invention. In order to ensure the correspondence between positioning marker 106 and moveable markers 110, the moveable markers 110 and positioning marker 106 by the surgical area are combined in the present invention and jointly fixed to a registered device 400, preferably such as but not limited to, a polyhedron in a pyramid-like shape, as shown in FIG. 13 and FIG. 14. In this embodiment, the registered device 400 has, such as but not limited to, a total of four surfaces including a first surface 401 on which a first positioning marker 106a is attached, for example, for a first user to view, a second surface 402 on which a second positioning marker 106b is attached, for example, for a second user to view, a third surface 403 on which a group of moveable markers 110 is mounted for a position tracker 108 to sense, and a fourth surface 404 on which a third positioning marker 106c is attached, for example, for a third user to view. By using the above configuration, a definitely unchanged relationship of position and an anchored mapping relationship for coordinate frames are thus established among positioning markers 106a, 106b, and 106c and moveable markers 110. The entire registered device 400 is preferably fixed to, for example, an extension rod 510 secured to, for example, a slidable side rail, configured on an operating table 500.

Therefore, by jointly configuring on the same registered device, the relative position relationships in a 3D space among multiple positioning markers 106a, 106b, and 106c and multiple moveable markers 110 are accordingly determined. Typically, multiple positioning markers 106a, 106b, and 106c and multiple moveable markers 110 have their own respective coordinate frames which are different from each other and require further coordinate transformations thereamong. When the relative spatial position relationships among multiple positioning markers 106a, 106b, and 106c and multiple moveable markers 110 are determined, predetermined, pre-defined, or preset (system default), for the MR device 200 and position sensor 108 to detect respectively, through jointly configuring on the same registered device, the surgical area (lesion) coordinate frame detected by the position tracker 108 is able to be sequentially transformed to a moveable marker coordinate frame through multiple moveable markers 110, and transformed to different positioning marker coordinate frames through multiple positioning markers 106a, 106b, and 106c. At last, respective MR device 200 detect respective positioning markers 106a, 106b, and 106c and in the meantime the respective MR device 200 acquires the exact location of surgical area computed by the computing unit module 116 performing a series of above-mentioned coordinate transformations, so that a virtual digital image model is capable of being aligned and corresponded to the surgical area in the reality.

Figure 15:
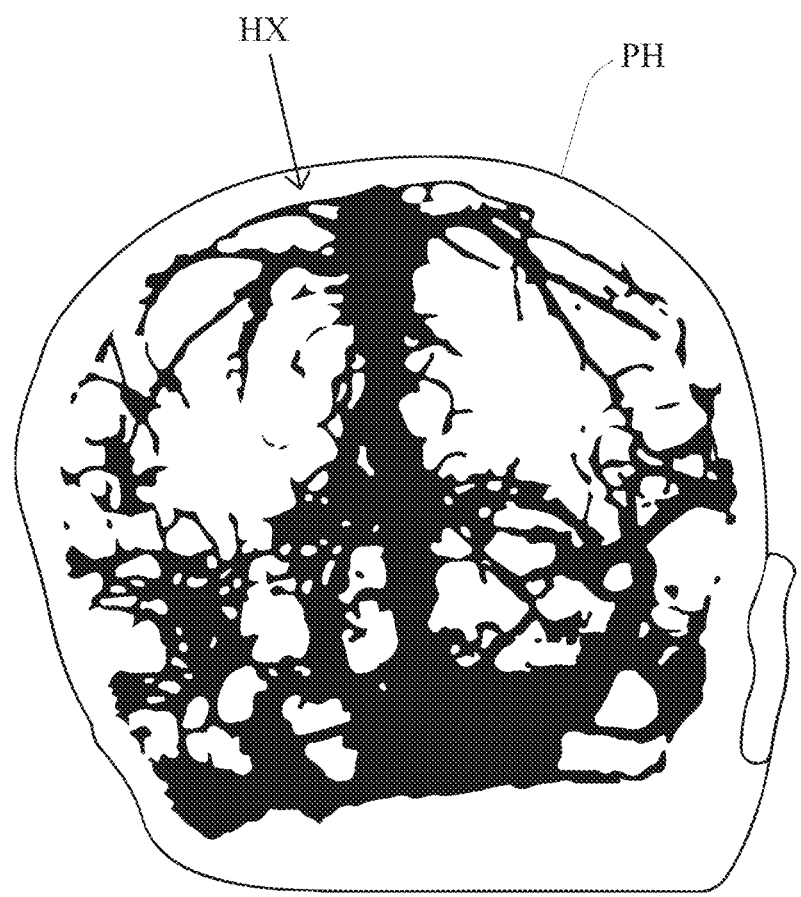
FIG. 15 is a diagram illustrating the overall MR images viewed by the user wearing the MR device and seeing through the MR device in accordance with the present invention.

FIG. 15 is a diagram illustrating the overall MR images viewed by the user wearing the MR device and seeing through the MR device in accordance with the present invention. FIG. 15 discloses a 3D cerebral blood vessel image model, the MR image is displayed by MR device after the aligning method and surgical area aligning of the present invention. In this embodiment, the surgical area is the head, so when the user wears the MR device, the visually seen images include the patient's head PH and the 3D cerebral blood vessel distribution image HX displayed on the MR device lens after surgical area aligning. As the 3D cerebral blood vessel distribution image HX has been accurately aligned to the surgical area, i.e. patient's head PH, after it is processed by the aligning method of the present invention, the user can directly see the MR of 3D cerebral blood vessel distribution image HX overlapped on the surgical area on the transparent display.

Figure 16:
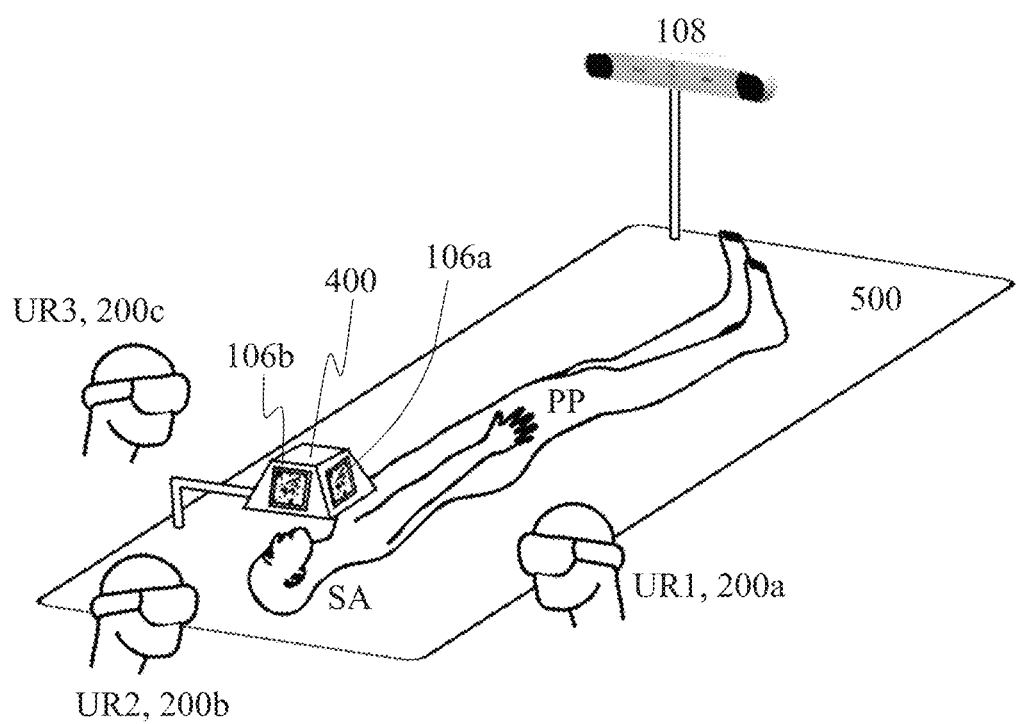
FIG. 16 is a diagram illustrating the scenario the aligning kit and method in accordance with the present invention provides for multiple users to operate.

FIG. 16 is a diagram illustrating the scenario the aligning kit and method in accordance with the present invention provides for multiple users to operate. When multiple surgeons participate in the surgery, multiple positioning markers 106a, 106b and 106c and multiple moveable markers 110 (incapable of being shown in FIG. 16 due to its position being on the back surface of and blocked by the registered device 400) is configured on a registered device 400 (for example, as shown in FIG. 13 and FIG. 14) in proximity to the surgical area SA of a patient PP. The positioning markers 106a, 106b and 106c (not shown in FIG. 16 due to being blocked) face toward users UR1, UR2 and UR3 respectively, and each of users UR1, UR2 and UR3 wear a MR device 200a, 200b and 200c respectively as well. The multiple moveable markers 110 mounted on the registered device 400 is configured to face toward the position tracker 108. When the registered device 400 is settled, the relative positions among multiple positioning markers 106a, 106b, and 106c, multiple moveable markers 110, and surgical area SA are determined accordingly and correspondingly. The entire registered device 400 is preferably fixed to an extension rod secured to a slidable side rail configured on an operating table 500.

The aligning kit and method proposed by the present invention performs coordinate transformation as aforementioned, to well cause the surgical area image model aligned and corresponded to the surgical area SA in real time, which the surgical area image model are displayed by MR devices 200a, 200b and 200b for the users UR1, UR2 and UR3 in different positions and orientations and at different angles and with different viewing angles to view in real time as well. Hence the multiple surgeons jointly participated in the surgery, in particular a sophisticated and complex surgery, work and operate synchronously. Due to the function provided by the registered device 400, even though either users UR1, UR2 or UR3 walks or moves around the patient PP or the surgical area SA during the entire surgery, the surgical area image model display on the screens in the respective MR devices 200a, 200b and 200b is dynamically and adaptively varied, in correspondence with, in interaction with, and in response to both the respective positions where users UR1, UR2 or UR3 walks or moves and the respective viewing angles that change all the time with the users UR1, UR2 or UR3' movement, so that no matter where either users UR1, UR2 or UR3 moves to or stays with, either users UR1, UR2 or UR3 can view the surgical area image model that is displayed with being correctly fitted with either users UR1, UR2 or UR3' current position and current viewing angle.

To sum up, the present invention uses two kinds of tracking markers with different functions. First kind of tracking marker is a fixed positioning marker, for mobile MR device to track. Second kind of tracking marker is a moveable marker, for the fixed optical tracker to perform real-time position tracking. With the two classes of markers, the system can determine the projection position of MR real-time dynamic 3D image model and provide MR real-time dynamic 3D image model for different viewing angles.

Based on the aligning technique proposed by the present invention, the MR device can accurately project the 3D image models containing the actual state of blood vessels, nerves and brain tissues onto the surgical area by real-time 3D visualization, which is displayed by the MR device for the surgeon, no matter how the surgeon moves during the operation, the 3D image displayed by the MR device is always positioned in the surgical area accurately, and the 3D images of surgical area at different viewing angles are displayed instantly and dynamically as the surgeon's viewing angle changes, which can be seen by multiple surgeons in different positions at different viewing angles, so that multiple surgeons can take part in the complex surgery synchronously.

The first kind of positioning marker with a characteristic pattern, locator and the second kind of moveable marker using an infrared ray to sense passive spherical marker are observed and sensed by the camera of MR/AR glasses and the position tracker respectively, the position and orientation relations of the camera to the characteristic pattern and spherical marker are worked out, the virtual instrument and virtual medical image are displayed by the display of MR/AR glasses on the real instrument and patient, so as to assist surgical navigation.

The aligning technique proposed by the present invention can be used the core technology in the MR surgical navigation system, the images of surgical area, patient and surgical instrument are displayed instantly by the MR glasses, assisting the surgeon to plan a safe surgical approach more intuitively, provide 3D surgical navigation and reduce the risks of cerebral arterial injuries of brain surgery.

Figure 17:
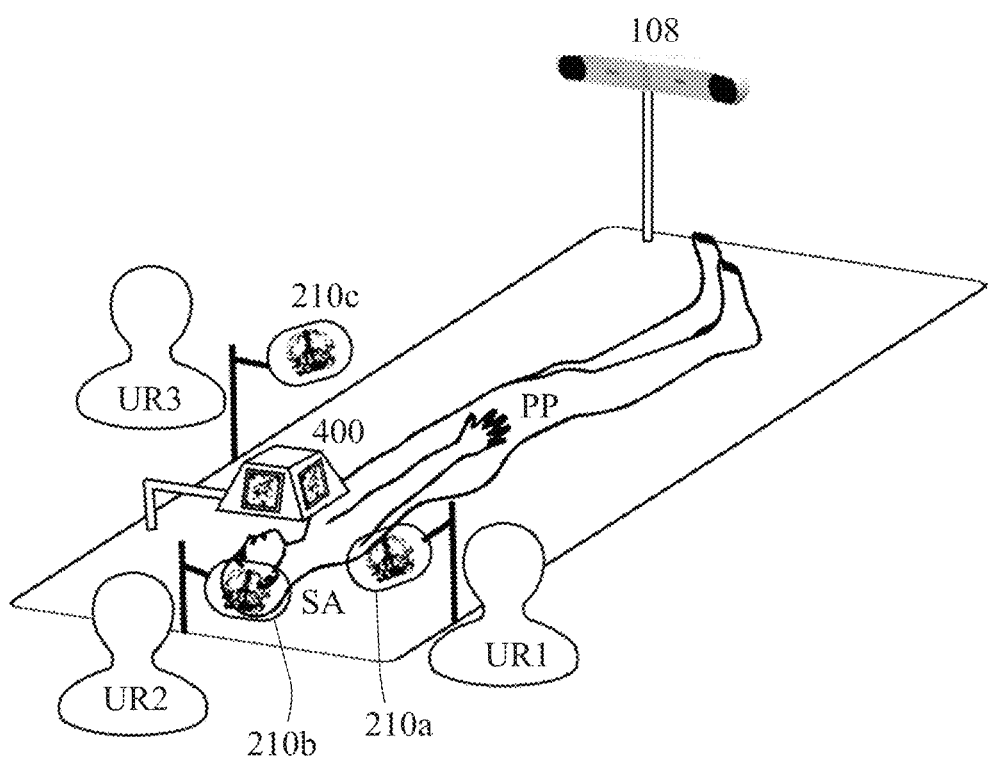
FIG. 17 is a diagram illustrating a second embodiment for implementing the present invention. In this embodiment, the see-through type displays 210a, 210b and 201c with AR sensors are replaced for the MR devices.

FIG. 17 is a diagram illustrating a second embodiment for implementing the present invention. In this embodiment, the see-through type displays 210a. 210b and 201c with AR sensors are replaced for the MR devices. Preferably, the see-through type displays 210a. 210b and 201c with AR sensors are adjustably secured to an extension rod secured to a slidable side rail configured on an operating table 500. Either users UR1, UR2 or UR3 stands in front of respective see-through type displays 210a, 210b and 201c with AR sensors, and freely adjust the position of respective see-through type displays 210a, 210b and 201c with AR sensors to until feeling comfortable to view. The AR sensors configured on the respective see-through type displays 210a, 210b and 201c commence detecting the positioning markers on the registered device 400 in proximity to surgical are SA and the position tracker 108 commence detecting moveable markers, so to as display the surgical area image model fitted with, and in correspondence with the current position of respective see-through type displays 210a, 210b and 201c for respective users UR1, UR2 and UR3 to view.

Figure 18:
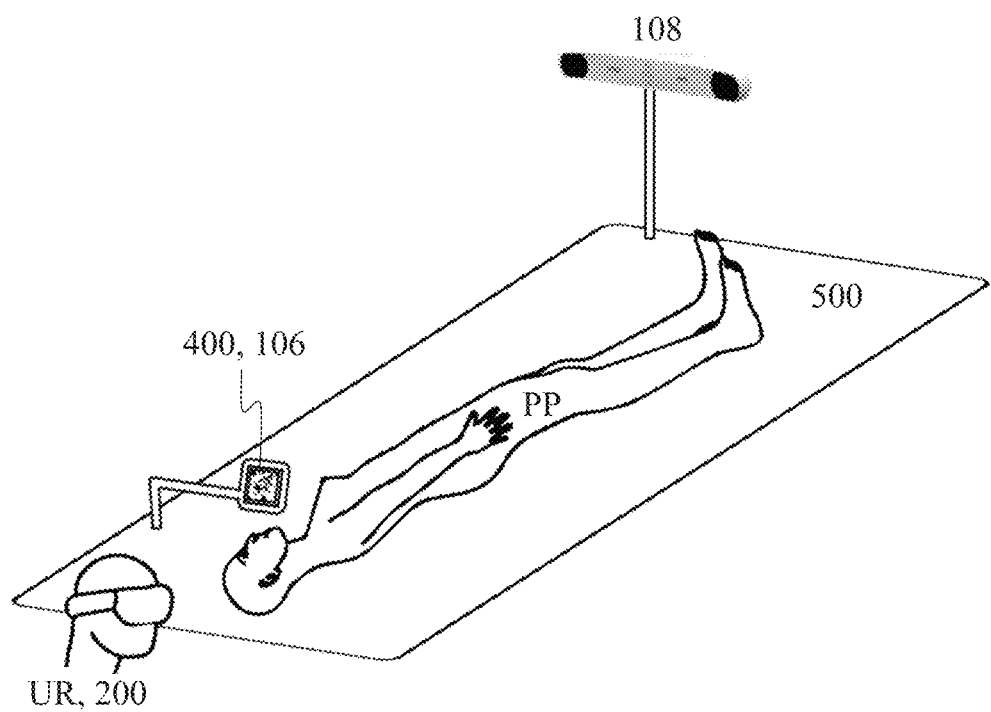
FIG. 18 is a diagram illustrating the scenario the aligning kit and method in accordance with the present invention provides for a single user to operate.

FIG. 18 is a diagram illustrating the scenario the aligning kit and method in accordance with the present invention provides for a single user to operate. In this embodiment, the registered device 400 is simply a flat tablet, to which the positioning marker 106 is attached, and secured to an extension rod secured to a slidable side rail configured on an operating table 500. When the single user UR moves, the surgical area image model is dynamically varied, in correspondence with, in response to, and to fit with the single user UR's current position and current viewing angle interactively, and is display on the screen of MR device 200 wore by the single user UR for the single user UR to view, due to the joint cooperation and function among the registered device 400, the positioning marker 106, the movable markers (not shown in FIG. 18), the position tracker 108, and the MR device 200.

There are further embodiments provided as follows.

Embodiment 1: A digital image reality aligning kit, applied to a mixed reality system integrated with a surgical navigation system, and includes: a plurality of moveable markers corresponded to a plurality of moveable marker coordinates respectively and a part of the plurality of moveable markers configured on a surgical instrument; a positioning marker corresponded to a positioning marker coordinate and configured in proximity to a surgical area corresponded to a surgical area coordinate, when the positioning marker is settled, the relative position thereof with respect to the other part of the plurality of moveable markers and the surgical area are determined accordingly, so as to transform the surgical area coordinate to the positioning marker coordinate: and a mixed reality device corresponded to a mixed reality device coordinate and detecting the positioning marker to transform the positioning marker coordinate to the mixed reality device coordinate accordingly, so as to project a surgical area digital image corresponded to a surgical area digital image coordinate onto the surgical area Embodiment 2: The digital image reality aligning kit as described in Embodiment 1, further includes: a position tracker corresponded to a position tracker coordinate and sensing the plurality of moveable markers, so as to transform the plurality of moveable marker coordinates and the surgical area digital image coordinate to the surgical area coordinate in accordance with the position tracker coordinate Embodiment 3: The digital image reality aligning kit as described in Embodiment 1, further includes one of devices as follows: a first registered device configured in proximity to a surgical area and having a first surface and a second surface fixed with the first surface, wherein the first surface provides for the positioning marker to configure and the second surface provides for the other part of the plurality of moveable markers to configure, and when the first registered device is settled in proximity to the surgical area, the relative positions among the positioning marker, the other part of the plurality of moveable markers, and the surgical area are determined accordingly: and a second registered device configured in proximity to a surgical area and having a plurality of surfaces, wherein one of the plurality of surfaces provides for the plurality of moveable markers to configure and others of the plurality of surfaces for the positioning marker to configure, and when the second registered device is settled in proximity to the surgical area, the relative positions among the positioning marker, the other part of the plurality of moveable markers, and the surgical area are determined accordingly.

Embodiment 4: The digital image reality aligning kit as described in Embodiment 1, when the positioning marker, the other part of the plurality of moveable markers, and the surgical area are settled, the relative positions thereamong are determined accordingly, and thus the relationship of the coordinate transformation among the positioning marker coordinate, the plurality of moveable marker coordinates, and the surgical area coordinate are determined and acts as a system default.

Embodiment 5: The digital image reality aligning kit as described in Embodiment 1, the surgical area digital image coordinate is transformed to the surgical area coordinate in accordance with the position tracker coordinate based on the plurality of moveable marker coordinates, to which the other part of the plurality of moveable markers correspond.

Embodiment 6: The digital image reality aligning kit as described in Embodiment 1, the surgical area digital image coordinate is transformed to the position tracker coordinate by implementing an image registration algorithm, the positioning marker coordinate is transformed to the mixed reality device coordinate by implementing a pinhole perspective projection positioning algorithm.

Embodiment 7: The digital image reality aligning kit as described in Embodiment 1, the surgical area digital image coordinate, the position tracker coordinate, the plurality of moveable marker coordinates, the positioning marker coordinate, the mixed reality device coordinate, and the surgical area coordinate are selected from one of a 2D Cartesian coordinate system, a 2D cylindrical coordinate system, a 2D spherical coordinate system, a 3D Cartesian coordinate system, a 3D cylindrical coordinate system, a 3D spherical coordinate system, and a combination thereof.

Embodiment 8: The digital image reality aligning kit as described in Embodiment 1, the surgical area digital image model is pre-constructed prior to an implementation of a surgery.

Embodiment 9: A digital image reality aligning method, applied to a mixed reality system integrated with a surgical navigation system, and includes: providing a plurality of moveable markers corresponded to a plurality of moveable marker coordinates respectively, a positioning marker corresponded to a positioning marker coordinate, a mixed reality device corresponded to a mixed reality device coordinate, and a surgical area corresponded to a surgical area coordinate: configuring a part of the plurality of moveable markers onto a surgical instrument; configuring the positioning marker and the part of the plurality of moveable markers in proximity to the surgical area and determining the relative positions among the surgical area, the positioning marker, and the part of the plurality of moveable markers, so as to transform the surgical area coordinate to the positioning marker coordinate: and detecting the positioning marker through the mixed reality device, to transform the positioning marker coordinate to the mixed reality device coordinate accordingly, and to project a surgical area digital image onto the surgical area.

Embodiment 10: The digital image reality aligning method as described in Embodiment 9, further includes one of steps as follows: providing a position tracker corresponded to a position tracker coordinate and the surgical area digital image corresponded to a surgical area digital image coordinate: determining a position of the position tracker and detecting the plurality of moveable marker by the position tracker, so as to transform the plurality of moveable marker coordinates, to which the part of the plurality of moveable markers correspond, and the surgical area digital image coordinate to the surgical area coordinate in accordance with the position tracker coordinate; and determining the relationship of coordinate transformation among the positioning marker coordinate, the plurality of moveable marker coordinates, to which the part of the plurality of moveable markers correspond, and the surgical area coordinate, by determining the relative positions among the surgical area, the positioning marker, and the part of the plurality of moveable markers.

While the disclosure has been described in terms of what are presently considered to be the most practical and preferred embodiments, it is to be understood that the disclosure need not be limited to the disclosed embodiments. On the contrary, it is intended to cover various modifications and similar arrangements included within the spirit and scope of the appended claims, which are to be accorded with the broadest interpretation so as to encompass all such modifications and similar structures. Therefore, the above description and illustration should not be taken as limiting the scope of the present disclosure which is defined by the appended claims.

What is claimed is:

1. A digital image reality aligning kit, applied to integrate a mixed reality system and a surgical navigation system, and comprising:
   a plurality of moveable markers corresponded to a plurality of moveable marker coordinates respectively and a part of the plurality of moveable markers configured on a surgical instrument;
   a registered positioning marker corresponded to a positioning marker coordinate and configured in proximity to a surgical area corresponded to a surgical area coordinate, when the registered positioning marker is settled, the relative position thereof with respect to the other part of the plurality of moveable markers and the surgical area are determined accordingly, so as to transform the surgical area coordinate to the positioning marker coordinate;

a registered device having a first surface configured with the registered positioning marker and a second surface configured with a part of the plurality of moveable markers and being placed at where is close to the surgical area;

a mixed reality device included in the mixed reality system corresponded to a mixed reality device coordinate and detecting the registered positioning marker to transform the positioning marker coordinate to the mixed reality device coordinate accordingly, so as to project a surgical area digital image corresponded to a surgical area digital image coordinate onto the surgical area; and a position tracker included in the surgical navigation system corresponded to a position tracker coordinate and sensing the plurality of moveable markers, so as to transform the plurality of moveable marker coordinates and the surgical area digital image coordinate to the surgical area coordinate in accordance with the position tracker coordinate, wherein the position tracker is disposed separately away from the mixed reality device, and the position tracker and the mixed reality device have respective sightlines, between which the respective sightlines an included angle in a range of 45° to 180° degrees is formed.

2. The digital image reality aligning kit as claimed in claim 1, further comprising one of devices as follows:

a first registered device configured in proximity to a surgical area and having a first surface and a second surface fixed with the first surface, wherein the first surface provides for the registered positioning marker to configure and the second surface provides for the other part of the plurality of moveable markers to configure, and when the first registered device is settled in proximity to the surgical area, the relative positions among the registered positioning marker, the other part of the plurality of moveable markers, and the surgical area are determined accordingly; and a second registered device configured in proximity to a surgical area and having a plurality of surfaces, wherein one of the plurality of surfaces provides for the positioning marker to configure and the other one of the plurality of surfaces provides for the other part of the plurality of moveable markers to configure, and when the second registered device is settled in proximity to the surgical area, the relative positions among the registered positioning marker, the other part of the plurality of moveable markers, and the surgical area are determined accordingly.

3. The digital image reality aligning kit as claimed in claim 1, wherein when the registered positioning marker, the other part of the plurality of moveable markers, and the surgical area are settled, the relative positions thereamong are determined accordingly, and thus the relationship of the coordinate transformation among the positioning marker coordinate, the plurality of moveable marker coordinates, and the surgical area coordinate are determined and acts as a system default.

4. The digital image reality aligning kit as claimed in claim 1, wherein the surgical area digital image coordinate is transformed to the surgical area coordinate in accordance with the position tracker coordinate based on the plurality of moveable marker coordinates, to which the other part of the plurality of moveable markers are corresponded.

5. The digital image reality aligning kit as claimed in claim 1, wherein the surgical area digital image coordinate is transformed to the position tracker coordinate by implementing an image registration algorithm, the positioning marker coordinate is transformed to the mixed reality device coordinate by implementing a pinhole perspective projection positioning algorithm.

6. The digital image reality aligning kit as claimed in claim 1, wherein the surgical area digital image coordinate, the position tracker coordinate, the plurality of moveable marker coordinates, the positioning marker coordinate, the mixed reality device coordinate, and the surgical area coordinate are selected from one of a 2D Cartesian coordinate system, a 2D cylindrical coordinate system, a 2D spherical coordinate system, a 3D Cartesian coordinate system, a 3D cylindrical coordinate system, a 3D spherical coordinate system, and a combination thereof.

7. The digital image reality aligning kit as claimed in claim 1, wherein the surgical area digital image is pre-constructed prior to an implementation of a surgery.

* * * * *